United States Patent
Hell et al.

(10) Patent No.: US 7,719,679 B2
(45) Date of Patent: May 18, 2010

(54) METHOD AND DEVICE FOR OPTICALLY MEASURING A SAMPLE

(75) Inventors: Stefan Hell, Göttingen (DE); Christian Eggeling, Göttingen (DE); Gerald Donnert, München (DE)

(73) Assignee: Max-Planck-Gesellschaft zur Förderung der Wissenschaften e.V., München (DE)

( * ) Notice: Subject to any disclaimer, the term of this patent is extended or adjusted under 35 U.S.C. 154(b) by 256 days.

(21) Appl. No.: 11/955,793

(22) Filed: Dec. 13, 2007

(65) Prior Publication Data

US 2008/0088839 A1    Apr. 17, 2008

Related U.S. Application Data

(63) Continuation-in-part of application No. PCT/EP2006/005765, filed on Jun. 15, 2006.

(51) Int. Cl.
*G01N 21/64* (2006.01)
(52) U.S. Cl. ....................................... 356/318
(58) Field of Classification Search ........................ None
See application file for complete search history.

(56) References Cited

U.S. PATENT DOCUMENTS

| | | | |
|---|---|---|---|
| 4,877,965 A * | 10/1989 | Dandliker et al. ........ 250/458.1 |
| 5,196,709 A | 3/1993 | Berndt et al. | |
| 6,707,556 B2 * | 3/2004 | Turner et al. ................. 356/436 |
| 6,741,344 B1 | 5/2004 | Stern et al. | |
| 7,253,893 B2 | 8/2007 | Hell et al. | |
| 2002/0027202 A1 | 3/2002 | Engelhardt et al. | |

FOREIGN PATENT DOCUMENTS

| | | |
|---|---|---|
| DE | 101 54 699 A1 | 5/2003 |
| EP | 0 636 914 B1 | 9/1998 |
| EP | 0 666 473 B1 | 5/2000 |
| EP | 0 632 887 B1 | 2/2002 |
| WO | WO 00/71028 A1 | 11/2000 |

* cited by examiner

*Primary Examiner*—Tu T Nguyen
(74) *Attorney, Agent, or Firm*—Thomas, Kayden, Horstemeyer & Risley, LLP

(57) ABSTRACT

The inventive method for optically measuring a sample consists in temporarily repeatedly transmitting an electromagnetic signal (2) to the sample in such a way that a substance contained in the sample is transferred from a first electronic state (1) into a second electronic state (3), wherein at least one part of said substance in the second state (3) emits photons which are used for carrying out the optical measurement of the sample, the signal (2) is transmitted to the same sample area at a certain repetition interval and said repetition interval of the signal (2) is adjusted with a lifetime of the second state (3) of the substance having an order of magnitude of 1 ns on a value of at least 0.1 μs which is optimized with respect to photon yield from the substance.

30 Claims, 3 Drawing Sheets

METHOD AND DEVICE FOR OPTICALLY MEASURING A SAMPLE

CROSS REFERENCE TO RELATED APPLICATIONS

This application is a continuation in part of International Patent Application PCT/EP2006/005765 entitled "Method and Device for optically Measuring a Sample", filed on Jun. 15, 2006, and claiming priority to co-pending German Patent Application No. DE 10 2005 027 896.5 entitled "Verfahren und Vorrichtung zum optischen Messen einer Probe", filed Jun. 16, 2005.

FIELD OF THE INVENTION

The invention generally relates to methods of optically measuring a sample. More particular, the invention relates to methods of optically measuring a sample including a substance which at least has a first electronic state and a second electronic state, the second electronic state being an excited electronic state of the substance, the second electronic state having a limited lifetime, and the substance emitting photons out of its second state, the method comprising the steps of: directing an electromagnetic signal at least one area of the sample to transfer the substance in the at least one area of sample out of its first electronic state into its second electronic state; and detecting photons emitted by at least a part of the substance out of its second state.

The electromagnetic signal for transferring the sample out of a first into a second state may particularly be light, and even more particularly laser light.

BACKGROUND OF THE INVENTION

A method of optically measuring a sample which is called STED microscopy is known from U.S. Pat. No. 7,253,893 B2. To the end of fluorescence microscopically examining a sample, a fluorescent dye or fluorophore in the sample is first transferred into an excited energetic state by means of excitation light. In this optical excitation, the usual limit for spatial resolution in optical methods of $\lambda/2n$ applies, $\lambda$ being the wavelength of the light used and n being the diffraction index of the sample. To get below this limit, the optically excited state of the fluorophore is de-excited with de-excitation light except of a desired measuring point in which the intensity distribution of the de-excitation light has a zero point; i.e. the fluorophore is forced to stimulated emission everywhere outside the actual measuring point by means of the de-excitation light. The dimensions of the resulting fluorescent measuring point, i.e. the spatial resolution of the remaining fluorescence, can significantly be lowered below the usual optical resolution limit in that the de-excitation light is applied to the sample outside of the desired measuring point at such a high intensity that saturation is achieved in de-excitation by means of stimulated emission. Thus, the fluorophore in the sample remains in its fluorescent state in a very narrowly delimited area about the zero point of the intensity distribution of the de-excitation light only. To cope with a limited average intensity of the de-excitation light, the de-excitation light and also the excitation light are pulsed. A further reason for using pulsed light in STED microscopy is to avoid that the intensive de-excitation light stresses the sample, even if the dye is not excited. Regarding a same area of the sample, irradiation with both the excitation and the de-excitation light is repeated multiple times at a short repetition interval which is sufficiently above the half-life of the fluorescent state of the fluorophore of typically 1 ns and has an order of magnitude of 10 ns to have a measurement signal sufficiently standing out of the background noise even with only few fluorophore molecules within a measuring point. Pulses of the excitation light and of the de-excitation light incident in the same areas of the sample comprise a typical repetition rate of 80 MHz.

With a high intensity of the de-excitation light which is necessary for saturation of the de-excitation outside the actual measuring point, there is a considerable probability that the dye in the sample bleaches, i.e. that it is chemically changed in such a way that it does no longer emit fluorescence light. Thus, the lifetime of the dye, i.e. the number of times at which fluorescence light from it may be registered from the fluorophore, is considerably reduced. This delimits the yield of fluorescence light from an actual sample in which naturally only a limited number of fluorophore molecules is available.

Similar problems with regard to the yield of photons in optically measuring a sample also occur with other fluorescence microscopic methods working with pulsed light, i.e. if high light intensities are employed, such as in multi-photon excitation, and also in other methods of optically measuring a sample, like for example in the lifetime measurement of fluorophores (life-time-imaging).

To enhance the yield of registered photons in methods of optically measuring a sample, high efforts have been spent to enhance the responsiveness of detectors to incident photons by which the photons from a sample are registered. An increase in responsiveness of high value detectors from about 20% up to 40 to 60% has been achieved within the previous 10 to 15 years. The associated increase of the yield of registered photons by a maximum factor of 3 was, however, accompanied by an extreme increase in cost of these detectors.

Despite the improvements with regard to the responsiveness of the detectors used, it is still the limited total yield of photons emitted by the fluorophore which sets the limits to most fluorescence-based measuring methods. In fluorescence microscopy, the limited number of photons emitted by a fluorophore in total, i.e. up to bleaching, nearly always is the main problem. Each considerable increase in the absolute signal by means of increasing the number of fluorescence light emissions prior to bleaching is of general importance for fluorescence microscopy.

A further method of optically measuring a sample which is called confocal two-photon microscopy is known from U.S. Pat. 2002/0027202 A1. In two-photon microscopy a quadratic dependency of the transition probability on the intensity distribution of the excitation light, which the fluorophore displays with regard to a transition out of its ground state into its excited fluorescent state upon taking up energy of two photons, is used for resolution enhancement. The excitation light is concentrated to pulses of high intensity to obtain an as high as possible yield of fluorescent light here. Due to the quadratic dependency of the transition probability of the fluorescence dye on the intensity of the excitation light, these pulses of high intensity result in more fluorescence light with a same average power of the excitation light as compared to a higher number of pulses of lower intensity. U.S. Pat. 2002/0027202 A1 additionally considers a negative effect on the fluorescence light yield which may result from a saturation of the excitation of the fluorescent state during each single pulse, and proposes to adjust the intensity of the pulses by means of keeping their repetition rate at a constant power of the excitation light so high that the negative influence on the fluorescence light yield does just not yet occur. The danger of bleaching of the fluorescence dye is not considered. As principally possible with regard to the repetition rate of the excitation light pulses U.S. Pat. 2002/0027202 A1 indicates a range of kHz to GHz, the repetition rate being to be adapted to the lifetime of the fluorescence dye; no numerical example, however, being given for this adaptation.

From EP 0666 473 B1 it is known to achieve a comparatively high yield of fluorescence light in two-photon microscopy despite the use of excitation light of comparatively low power in that very special fluorescence dyes, like for example lanthanide chelates, which have a long average lifetime of at least 0.1 µs ($1 \times 10^{-7}$ s), are subjected to comparatively long pulses of excitation light adapted to these lifetimes. The repetition rate of these long pulses is lower than 10 MHz ($1 \times 10^7$ Hz) which corresponds to the indicated lifetime in the usual way.

The lifetime of the fluorescent state of fluorescence dyes usually used in fluorescence microscopy, however, is in the order of magnitude of 1 ns, i.e. shorter than 10 ns.

There is the need of a method of optically measuring a sample by which a considerable increase in the yield of registered photons can be achieved without a further expensive increase of the responsiveness of the detectors used.

SUMMARY OF THE INVENTION

In a first aspect, the present invention relates to a method of optically measuring a sample including a substance which at least has a first electronic state and a second electronic state, the second electronic state being an excited electronic state of the substance, the second electronic state having a limited lifetime, and the substance emitting photons out of its second state, the method comprising the steps of: selecting the substance in the sample from a group of substances having a lifetime of the second state of the substance in an order of magnitude of 1 ns; repeatedly temporally directing an electromagnetic signal having a repetition interval of time at least one area of the sample to transfer the substance in the at least one area of sample out of its first electronic state into its second electronic state; optimizing a value of the repetition interval of time of the signal with regard to a yield of photons from the substance, the optimized value being at least 0.1 µs with the lifetime of the second state having an order of magnitude of 1 ns; and detecting photons emitted by at least a part of the substance out of its second state.

In a more detailed aspect, the present invention relates to a method of optically measuring a sample including a substance which at least has a first electronic state and a second electronic state, the second electronic state being an excited electronic state of the substance, the second electronic state having a limited lifetime, and the substance emitting photons out of its second state, the method comprising the steps of: selecting the substance in the sample from a group of substances having a lifetime of the second state of the substance which is longer than 0.1 ns and shorter than 10 ns; repeatedly temporally directing an electromagnetic signal having a repetition interval of time at n separate spatially limited areas of the sample at one time to transfer the substance in each of these n areas of the sample out of its first electronic state into its second electronic state; optimizing a value of the repetition interval of time of the signal with regard to a total yield of photons obtainable from a certain amount of the substance, the optimized value being at least 1 µs with the lifetime of the second state having an order of magnitude of 1 ns, the optimized value of the repetition interval of time of the signal being longer than a lifetime of a third state of the substance into which a considerable part of the substance in the areas of the sample of at least $1 \times 10^{-4}$ is transferred during one repetition of the electromagnetic signal in a parasitic way, the lifetime of the third state being longer than the lifetime of the second state of the substance by at least one order of magnitude, and the substance being transferable with the electromagnetic signal out of its third state into a fourth state out of which the substance does neither return into the first state nor into the second state for an interval of time which is longer than the 100-fold of the lifetime of the third state, and a repetition frequency of the electromagnetic signal at which it is directed at any areas of the sample in optically measuring the sample is at least 100 kHz/n; and detecting photons emitted by at least a part of the substance out of its second state.

In a further more detailed aspect, the present invention relates to a method of optically measuring a sample including a substance which at least has a first electronic state and a second electronic state, the second electronic state being an excited electronic state of the substance, the second electronic state having a limited lifetime, and the substance emitting photons out of its second state, the method comprising the steps of: selecting the substance in the sample from a group of substances having a lifetime of the second state of the substance which is longer than 0.1 ns and shorter than 10 ns; scanning the sample with an electromagnetic signal directed at least one spatially limited area of the sample to transfer the substance in the at least one spatially limited area of sample out of its first electronic state into its second electronic state; optimizing a value of a repetition interval of time at which the electromagnetic signal is directed at the same area of the sample with regard to a total yield of photons obtainable from a certain amount of the substance, the optimized value being at least 0.1 µs with the lifetime of the second state having an order of magnitude of 1 ns, and the optimized value of the repetition interval of time of the signal being longer than a lifetime of a third state of the substance into which a considerable part of the substance in the areas of the sample of at least $1 \times 10^{-4}$ is transferred during one repetition of the electromagnetic signal in a parasitic way, the lifetime of the third state being longer than the lifetime of the second state of the substance by at least one order of magnitude, and the substance being transferable with the electromagnetic signal out of its third state into a fourth state out of which the substance does neither return into the first state nor into the second state for an interval of time which is longer than the 100-fold of the lifetime of the third state; and detecting photons emitted by at least a part of the substance out of its second state.

Surprisingly, it turns out that the yield of photons from a fluorescent substance reaches an optimum at an optimized repetition interval of the electromagnetic signal which is clearly longer than the lifetime of the excited second state of the substance out of which it emits the photons. It seems to be that further electronic states of the substance are directly or indirectly excited by the signal, which have a longer lifetime and which should reasonably decay before the electromagnetic signal is once again directed at the substance in the same area of the sample. Thus, turning away from the previous approach to increase the yield of photons in that dead times in optically measuring the sample are avoided by means of an as short as possible repetition interval, i.e. by a repetition interval approximating the lifetime of the photon-emitting state of the substance, is necessary. In the present invention, a reasonable level of dead time between two repetitions of the signal is accepted, and the yield of photons from the substance is even increased in this way. It will be appreciated that it is not suitable to extend the repetition interval arbitrarily here, as this would be at the expense of the total duration of the optical measurement. Thus, the optimized repetition interval is a compromise between a maximum yield of photons from the substance and an adequate total duration of the optical measurement.

If the repetition interval is varied in a range from at least 0.1 µs up to 2 µs, the strongest increase in the yield of photons from the substance by increasing the repetition interval is covered.

In varying the repetition interval, the energy of each signal can be kept constant. However, this is not imperative. Instead, the energy of each single signal may typically be clearly increased with the optimized repetition interval as compared to shorter repetition intervals, without an increased danger of bleaching the substance with the signal.

The optimization of the repetition interval can be executed based on different aspects of the considered yield of photons from the substance. If the observed yield of photons from the substance is the yield of photons from the substance obtained with a certain number of repetitions of the signal, like for example the yield of photons per repetition of the signal, there will typically be an increase of the yield of photons with any increase of the repetition interval. The criteria for the optimized repetition interval may then be achieving a particular percentage of for example 90% of an absolute maximum yield.

If the observed yield of photons from the substance is the yield of photons from the substance obtained during a certain duration of the optical measurement of the sample, the optimized repetition interval is that one at which the maximum yield within the predetermined period of time is achieved.

The observed yield of photons from the substance may also be the yield of photons which can all at all be obtained from the substance, i.e. up to its bleaching. In this total yield of photons from the substance an increase with any increase of the repetition interval may be expected again; correspondingly, the criteria for the optimized repetition interval may be achieving a certain percentage of for example 90% of an absolute maximum total yield of photons from the substance.

It will be appreciated that the optimized repetition interval determined according to the invention will be preferably be adjusted for the further optical measurement of the sample. In a new apparatus or microscope used for executing the new method, this may occur automatically, or an optimization device may output one optimized repetition interval or a plurality of optimized repetition intervals optimized according to different criteria, one of which is selected by the user of the device and then adjusted by the optimization device or the user himself in an adjustment device for the voluntary adjustment of the repetition interval for the further optical measurement of the sample.

In a particular aspect of the new method, an optimized repetition interval of time at which the electromagnetic signal, for example an optical light signal, is repeatedly temporarily directed at the same areas of the sample to transfer a substance in the sample out of a first into a second electronic state is longer than a lifetime of a third state into which a considerable part of the substance in the sample is transferred due to the electromagnetic signal in a parasitic way. Particularly, the repetition interval of time may be determined with regard to the lifetime of such a third state out of which the substance may be transferred by the signal into a fourth state out of which it does not return into the first or second state for a period of time which is longer than the length of the optical measurement. The present invention is based on the surprising finding that a considerable danger of inactivation of the substance in the sample is due to the substance being transferrable out of a third state, into which it gets in a parasitic way and out of which it normally gets back quite soon into the first or second state, into a fourth state out of which it does not return for a long time or not at all into the first or second state. A dye molecule which persistently stays in the fourth state or which is chemically amended out of the fourth state may be called "bleached" as it will no longer be able to contribute to the fluorescence light emitted by the sample. In such processes very small probabilities are sufficient to transfer a great portion of the substance in the sample into the fourth state and thus inactivate it persistently by frequently repeatedly directing the electromagnetic signal at the same areas of the sample. If, however, the repetition interval of the signal is, according to the teaching of the present invention, set longer than the lifetime of the third state, no relevant portion of the substance is still in the third state when the electromagnetic signal is directed at the sample for the next time. Thus, no relevant parts of the substance may be transferred out of the third state into the fourth state during the repetition of the signal and thus be inactivated in this way.

The considerable proportion of the substance getting in the third state may be apparently very small with a part of $1\times10^{-2}$ down to $1\times10^{-4}$ of the sample being transferred into the third state upon one incident of the electromagnetic signal. Due to the typically very high number of repetitions of the electromagnetic signal during measuring one area of the sample, even such a small proportion of the substance which is transferred into the third state will considerably increase the danger of bleaching the substance, if for example the lifetime of the third state is clearly longer than the effective lifetime of the first or second state so that the substance is accumulated in the third state. Naturally, bleaching of the substance is also increased, if the probability at which the signal transfers the substance out of the third into the fourth state is comparatively high.

Such fourth states into which the substance may get due to the electromagnetic signal out of the third state and out of which the substance does not get back into the first or second states for a period of time which is longer than 1 minute, particularly longer than 10 minutes and even more particularly longer than 1 hour, are of particular relevance for that aspect of the present invention explained here. A return or non-return of the substance out of the fourth state into the first or second state after this period of time is normally no longer relevant for the optical measurement of the sample according to the present invention, as at least considerable portions of the substance potentially remain in the fourth state so long that they are no longer practically available for the optical measurement of the sample during the optical measurement. In so far as a lifetime of the third state or a period of time for which the substance does not get back out of the fourth state into the first or second state are mentioned here, the respective half-lifetimes of the third or fourth state, respectively, are meant. It is clear to those skilled in the art that even with a very long half-life parts of the substance leave the respective state much earlier or also much later, as these processes are based on transition probabilities which do not result in transitions at certain points of time.

Although the measure of the present invention to increase the repetition interval at which the signal is directed to the same areas of the sample up to reaching an optimum appears to be simple and in fact requires no high technical efforts in its application in microscopy, the effects of the invention are surprisingly great. The yield of photons in methods of optically measuring a sample, in which a fluorescence dye in the sample is subject to high light intensities in each repetition of a repeated electromagnetic signal, may actually be increased tenfold. Particular examples for the beneficial application of the method are STED microscopy as described in U.S. Pat. No. 7,253,893 B2 in which the de-excitation light has a particular high intensity, and fluorescence microscopy with multi-photon excitation, in which very high light intensities have to be used, too. General advantages, however, also result in other methods of optically measuring a sample, like for example in lifetime imaging with pulsed light.

It is important to indicate that the electromagnetic signal, like for example a light signal, may, within the scope of the present invention, comprise different components, like for example portions of different wavelengths or different parts following each other in time. By means of the invention, the repetition interval of the electromagnetic signal is determined, at which the electromagnetic signal is repeatedly directed at the sample for once optically measuring at least one measuring point.

The optimized repetition interval of the electromagnetic signal is at least 0.1 µs in the present invention. This corresponds to a maximum repetition rate at which the signal is directed at the same areas of the sample of 10 MHz. It is preferred, if the repetition interval of the electromagnetic signal is at least 1 µs. This corresponds to a repetition rate of less than 1 MHz. In determining the repetition rates corresponding to the repetition intervals, the duration of the respective electromagnetic signal has also to be considered, so that a slightly lower value than the reciprocal value of the repetition interval results for the repetition rate.

As already indicated, it makes no sense in the present invention to arbitrarily reduce the repetition frequency at which the electromagnetic signal is directed at any areas of the sample to optically measuring it. As a result, the duration of the optical measurement, within which a certain absolute yield of photons is achieved, would considerably be increased so that, for example, the signal to noise ratio could strongly be deteriorated or stability problems could occur. Thus, it is preferred, if the repetition frequency of the electromagnetic signal is at least 100 kHz. A considerably lower repetition frequency could, however, be accepted, if the sample is simultaneously optically measured in a number n of measuring point, as the yield of photons per time is then increased by a factor n. Correspondingly, the repetition frequency of the signal may be reduced down to 100 kHz/n. If the sample is, for example, covered all over by the electromagnetic signal and observed by a camera, the number of the pixels of the camera may be regarded as n, so that n may even be quite high. By means of a reduction of the repetition frequency proportional to 1/n, however, no relevant advantages with regards to the maximum yield of photons from the substance in the sample up to its bleaching are obtained, at least with higher values of n. These advantages occur already with an increase of the repetition interval of the electromagnetic signal up to about 0.1 µs to 10 µs depending on the particular substance.

For actually applying the present invention, a repetition frequency of the optical signal which is directed at the sample may be tuned downwards to increase the repetition interval. Such a repetition frequency usually is in the order of magnitude of 80 MHz with most present optical methods in which an optical signal is repeatedly directed at a sample. For carrying out the invention, this repetition frequency is, for example, lowered down to 500 kHz.

If the electromagnetic signal is at any one time only directed at a spatially limited area of the sample, and if the sample is scanned with the electromagnetic signal or the spatially limited area, a scanning velocity at which the sample is spatially scanned may also be increased instead of reducing the repetition frequency of the electromagnetic signal to increase the repetition interval in time. Both measures, i.e. the reduction of the repetition frequency and the increase of the scanning velocity may also be used simultaneously to raise the repetition interval to a value according to the invention. It is important that the repetition interval at which the same area of the sample is repeatedly subjected to the electromagnetic signal stays above the minimum according to the present invention. Scanning the sample with the electromagnetic signal at such a high velocity that two consecutive repetitions of the electromagnetic signal do not cover the same area of the sample so that the areas subjected to the optical signal at any one time do not overlap contributes to this end. In this case, the repetition interval at which the electromagnetic signal is directed at the sample may become very high without a decrease in the yield of photons per time unit.

If the sample is scanned with the electromagnetic signal, the photons from the sample are preferably registered with a one or two dimensional light sensor array onto which at least a part of the sample is invariantly imaged. Each spatially limited area of the electromagnetic signal moving with regard to the sample in scanning the sample is just consecutively imaged on other light sensors of the light sensor array, the same light sensor, however, always registering photons out of the same area of the sample. Thus, the high speed scanning of the sample according to the invention is not associated with problems in separating photons out of different areas of the sample. The light sensor array may be a camera, particularly an electronic camera, like for example a CCD or CMOS camera.

With a sufficiently high speed of scanning the sample with the electromagnetic signal the signal may even comprise a continuous part or all at all be a continuous signal which, however, due to the high scanning velocity at which the sample is scanned, is only temporarily directed at the individual areas of the sample. The optical signal may thus completely or partly originate from a continuous wave laser.

The increase in signal due to high speed scanning with a very high scanning velocity is also surprising to those skilled in the art, as those skilled in the art would not expect any advantage of scanning the sample at a higher speed as such. This wrong expectation is promoted by the wrong conception that it is necessary to measure at every one point of the sample for such a long time that sufficient signal has been collected. The high speed scanning thus appears at first only as an unnecessary burden to those skilled in the art.

The new method may be applied in the field of fluorescence microscopy. Particularly, the signal may comprise excitation light and de-excitation light for excitation and spatially limited de-excitation of the substance in a STED method. The signal may also comprise excitation light for excitation, particularly multi-photon excitation, of a fluorescence dye and more generally of a fluorophore as the substance in the sample.

The second state into which the substance is transferred by means of the electromagnetic signal and out of which it emits photons may also be a virtual state (non-eigen-state) of a molecule in the sample, which has a very small lifetime (<1 fs) but which is nevertheless involved in a (non-linear) scattering process of the incident electromagnetic signal, the scattered light generated by means of the (non-linear) scattering process being used as the measuring signal. Such nonlinear scattered light inter alia includes higher harmonics (second and third harmonics) and Coherent Antistokes Raman Scattering (CARS).

The course of the intensity of the electromagnetic signal which is repeatedly directed at the sample with the repetition interval according to the invention may be variable. It may both consist of one single pulse or of a plurality of single or individual pulses. The latter option does not only refer to the combination of pulses of different wavelengths already mentioned. Each repetition of the signal may also comprise several individual pulses of the same wavelength, like for example in form of bursts, in which the frequency of the individual pulses has a usual high order of magnitude of 100 MHz or more. The number of the individual pulses of the same wavelength in the signal may be in a range of 2 to 100 here. However, it is important, that the signal terminates and the repetition interval starts, when a relevant part of the substance has already been transferred into the third state mentioned above over the preceding signal. If the transition probability into the third state is small, the number of the individual pulses of the same wavelength in each repetition of the signal may also be higher than 100. In each case the fraction of the substance in the third state has sufficient time to decay during the following repetition interval.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
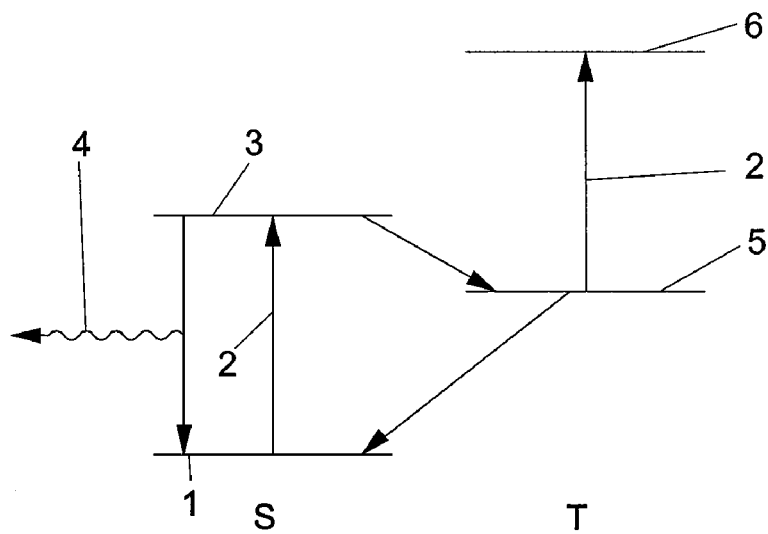
FIG. 1 shows various electronic energy states of a fluorescence dye.

Referring now in greater detail to the drawings, FIG. 1 schematically illustrates electronic states of a fluorescence dye or fluorophore. These electronic states include a ground state 1 which corresponds to the lowest energy of the fluorescence dye in its singulett state S and at all. By means of an electromagnetic signal 2, the fluorescence dye can be transferred into an excited state 3, which also belongs to the singulett state S of the fluorescence dye and which may be the fluorescent state of the fluorescence dye of interest here, out of which it can return into the ground state 1 under emission of registerable fluorescence light 4. Further, there is a certain probability, that the fluorescence dye gets into a third state 5 due to the electromagnetic signal 2, which is the state with the lowest energy within the triplet state T of the fluorescence dye here. It is indicated in FIG. 1, that the fluorescence dye gets into the state 5 out of the state 3. It is also possible, however, that the fluorescence dye directly gets out of the state 1 into the third state 5 excited by the signal 2. If a lifetime which determines a return of the fluorescence dye out of the third state 5 into the ground state 1 or even into the excited state 3, is longer than a repetition interval of the signal 2, the state 5 is pumped up in case of a rapid repetition of the signal 2 up to a certain level which is determined by the exact interrelations of the transition probabilities into the state 5, the lifetime of the state 5 and the repetition interval of the signal 2. I.e. a certain part of the molecules of the fluorescence dye of typically a few percent is always in the state 5 and is thus transiently not available for the emission of fluorescence light 4. These molecules of the fluorescence dye in the state 5 are nevertheless in principle still available and emit fluorescence light 4 again after their return into the state 1 or 3. Thus, the fluorescence dye in the state 5 needs not to be regarded as bleached, i.e. as no longer available for optically measuring a sample. The situation is different with regard to fractions of the fluorescence dye which may get out of the third state 5 due to excitation by the signal 2 into a fourth state 6, out of which they no more get in to the ground state 1 or the excited state 3, because either the fourth state 6 has a very long lifetime or a chemical change, i.e. a destruction of the fluorescence dye, occurs out of the fourth state 6.

The typical lifetime of the fluorescence state 2 of fluorescence dyes is in the order of magnitude of 1 ns. The lifetime of the state 5 observed here is typically at least one order of magnitude higher. The half-life at which the fluorescence dye gets out of the state 6 either via the state 5 or via another way into one of the states 1 and 3, if it gets back at all, is longer by some powers of ten so that even numerically small probabilities that the fluorescence dye gets into the state 5 and out of the state 5 into the state 6 have a substantial influence on the number of times in which the fluorescence dye will emit fluorescence light before it is bleached, i.e. inactivated in any way.

The loss of the fluorescence dye, because it get into the state 6, is, however, inhibited according to the invention in that a repetition interval of the signal 2 is extended beyond the lifetime of the third state 5. Thus, not relevant occupation of the state 5 still occurs, on the one hand, and as a result the danger that relevant parts of the fluorescence dye which are in the state 5 are subjected to the signal 2 and thus get into the state 6 is avoided, on the other hand.

Figure 2:
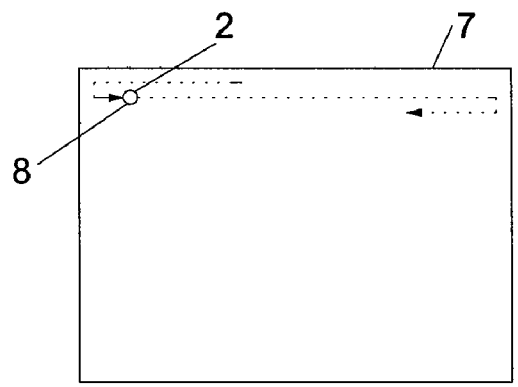
FIG. 2 sketches a step of scanning a sample with a single measuring point in optically measuring a sample.

As in contemplation of the repetition interval of the signal 2 only the same molecules of the fluorescence dye are relevant, i.e. that the signal 2 does not hit the same areas of a sample with a too high repetition rate, the area of the sample onto which the signal 2 is directed may be changed so quickly that the signal 2 does not hit the same areas of the sample with its own repetition frequency, instead of increasing the repetition interval of the signal 2 which directly corresponds to a reduction of its repetition frequency. FIG. 2 sketches the step of scanning a sample 7 with a measuring point 8 which corresponds to the area in which the sample 7 is subject to the signal 2. If the measuring point 8 is moved over the sample 7 so quickly in the indicated direction that the signal 2 in each of its repetitions does not hit the same area of the sample 7 as before, a same effect is achieved as with reducing the repetition frequency of the signal 2 itself. With a sufficient fast movement of the measuring point 8 over the sample 7, the signal 2 may even be a continuous signal and still have the effect of a temporary signal in each individual measuring points 8.

Figure 3:
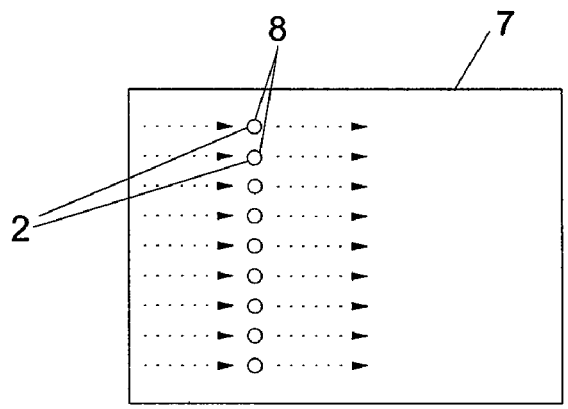
FIG. 3 sketches a step of scanning a sample with a multitude of measuring points in optically measuring the sample.

FIG. 3 indicates how an increase in the number of the measuring points 8 with which the sample 7 is scanned, may even then increase the total yield of photons per time unit, when the repetition frequency of the signal 2 is reduced for each of the measuring points 8. In case of the depicted ten measuring points 8, the repetition frequency of the signal 2 in each measuring point 8 may be reduced to a tenth without producing a loss in the total fluorescence light from the sample 7 excited by means of the signal 2 according to FIG. 1 as compared to a single measuring point 8 in which the repetition frequency is not reduced. As the yield of photons in each measuring point 8 does only decrease less than proportionally with the described reduction of the repetition frequency of the signal 2, as the relative part of the fluorescence dye is reduced which gets into the state 5 or the state 6 according to FIG. 1, the yield of photons per time unit with ten measuring points instead of one measuring point with a tenfold frequency of the signal 2, is even principally higher. This difference even increases with time, as in the invention nearly no molecules of the fluorescence dye still get into the state 6 and are thus lost for optically measuring the sample 7.

It belongs to the teaching of this invention that a repetition rate of the incident electromagnetic signal which is characteristic for the sample provides a maximum total yield of photons. This can also be a repetition rate range in which an absolute maximum total yield of photons is completely or at least essentially obtained. Within this repetition rate range, however, it is preferred to select the highest possible repetition rate at which not only the total fluorescence yield is high but at which the total measuring time is also as short as possible.

Figure 4:
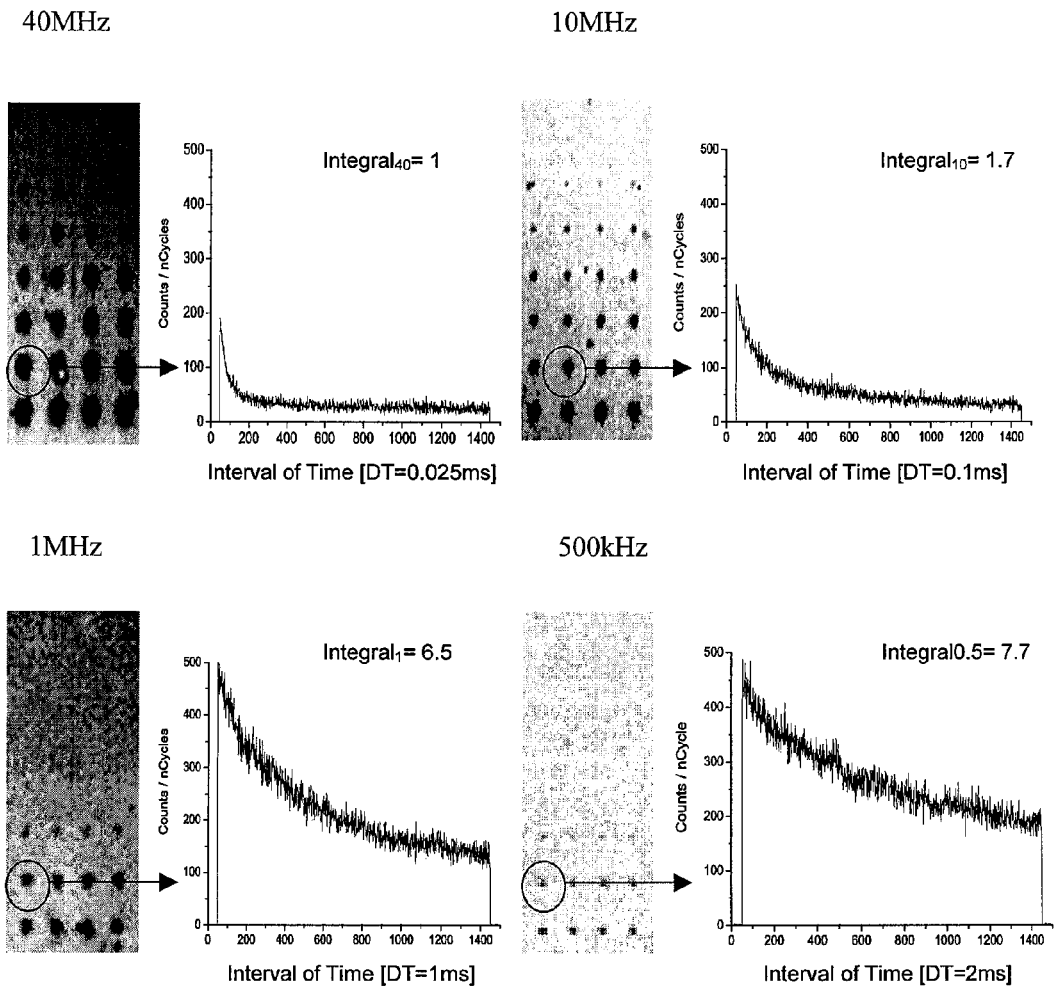
FIG. 4 shows an increase in a total yield of photons in pulsed excitation of a usual fluorophore with 1-photon absorption at 470 nm, and at a fixed pulse duration of 100 picoseconds by a factor of 7.7 upon reducing the repetition frequency from 40 MHz to 500 kHz.

The measurement series for the dye Atto532 (excitation wavelength 470 nm; 1-photon-absorption) shown in FIG. 4 reveals that a repetition rate of 500 kHz-1 MHz is a good choice. At this repetition rate the total yield of photons from the fluorescence of the dye is increased by a factor of 6.5 to 7.7 as compared to a repetition rate of 40 MHz which is typical for the prior art.

The measurements for determining the maximum yield of photons from the fluorescence of the dye Atto532, the results of which are depicted in FIG. 4, have been executed with a fixed Atto532 dye layer in a raster block pattern of 32 different points (4×8). In this block the excitation light power is downwardly doubled per line, so that the darkest stains correspond to the highest laser power. The increase in the power and the raster as such, however, are not important here. It is important, that the raster block was recorded with different laser pulse rates: 40 MHz, 10 MHz, 1 MHz and 500 kHz. The recording time at every point was adjusted according to the repetition rate so that each point was hit by the same total number of pulses ($1.4 \times 10^6$ pulses). Overall, merely the interval between the pulses has been varied but not the integral radiation load. The maximum power was 40 µW at 40 MHz. The time courses indicate the fluorescence yield at a fixed place of the sample at a same peak power and at a same total number of pulses hitting the dye molecule measured at the four laser pulse repetition rates. The integral over the measuring time indicates the increase of the fluorescence yield by the factor of 7.7 between the measurement at 40 MHz and the measurement at 500 kHz. At the same time, the reduction of the dye bleaching with the reduction of the repetition rate is evident in the pictures.

Figure 5:
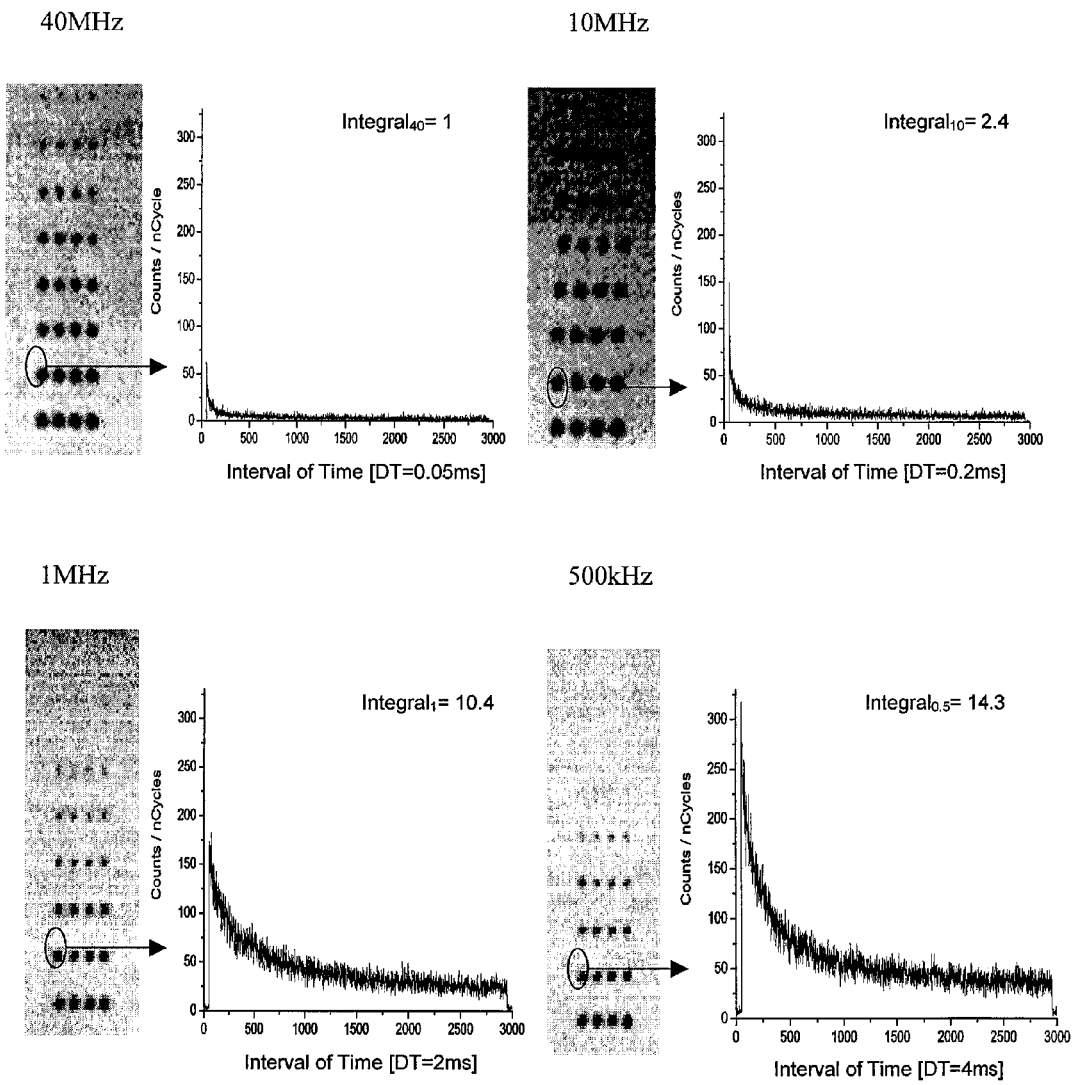
FIG. 5 shows an increase in the total yield of photons in pulsed excitation of green fluorescent protein (GFP) with 2-photon absorption at 900 nm, and at a pulse duration of about 200 femtoseconds by a factor of 14.3 upon reducing the repetition frequency from 40 MHz to 500 kHz.

It appears from FIG. 5 that in case of the green fluorescent protein (GFP) which is a very important fluorophore in fluorescence microscopy with 2-photon-excitation at a wavelength of 900 nm even an increase in the total yield of photons by a factor of 10-14.3 is achieved due to setting the repetition rate of the excitation light pulses in the range of 500 kHz to 1 MHz instead of at the usual 40 MHz.

The measurements, the results of which are depicted in FIG. 5, have been carried out at a fixed layer of the green fluorescent protein (GFP). As with the preceding results according to FIG. 4 measurements were made at equal peak power and with a recording time adjusted to the repetition rate and the same number of $1.4 \times 10^6$ pulses (maximum power 4 mW at 40 MHz). Optimization of the repetition interval of the pulses resulted in an increase in the yield of photons from GFP by a factor of 14.3 when comparing the measurements at 40 MHz and at 500 kHz. The reduction of the fluorophore bleaching can be also be directly proved in this case by means of the bleaching images.

Many variations and modifications may be made to the preferred embodiments of the invention without departing substantially from the spirit and principles of the invention. All such modifications and variations are intended to be included herein within the scope of the present invention, as defined by the following claims.

LIST OF REFERENCE NUMERALS 1 ground state
2 signal
3 state
4 fluorescence light
5 state
6 state
7 sample
8 measuring point

We claim:

1. A method of optically measuring a sample including a substance which at least has a first electronic state and a second electronic state, the second electronic state being an excited electronic state of the substance, the second electronic state having a limited lifetime, and the substance emitting photons out of its second state, the method comprising the steps of:

selecting the substance in the sample from a group of substances having a lifetime of the second state of the substance in an order of magnitude of 1 ns;

repeatedly temporally directing an electromagnetic signal having a repetition interval of time at least one area of the sample to transfer the substance in the at least one area of sample out of its first electronic state into its second electronic state;

optimizing a value of the repetition interval of time of the signal with regard to a yield of photons from the substance, the optimized value being at least 0.1 µs with the lifetime of the second state having an order of magnitude of 1 ns; and detecting photons emitted by at least a part of the substance out of its second state; wherein the optimized value of the repetition interval of time of the signal is longer than a lifetime of a third state of the substance into which a considerable part of the substance in the sample is transferred due to the electromagnetic signal in a parasitic way, the lifetime of the third state being longer than the lifetime of the second state of the substance by at least one order of magnitude, and the substance being transferable with the electromagnetic signal out of its third state into a fourth state out of which the substance does neither return into the first state nor into the second state for an interval of time which is longer than the 100-fold of the lifetime of the third state.

2. The method of claim 1, wherein the substance in the sample is selected from a group of substances having a lifetime of the second state of the substance which is longer than 0.1 ns and shorter than 10 ns.

3. The method of claim 1, wherein the substance in the sample is selected from a group of substances having a lifetime of the second state of the substance which is between 0.5 and 5 ns.

4. The method of claim 1, wherein the yield of photons from the substance with regard to which the value of the repetition interval of time is optimized is the total yield of photons obtainable from a certain amount of the substance within a certain amount of time.

5. The method of claim 1, wherein the considerable part of the substance which is transferred into the third state during one repetition of the electromagnetic signal is at least $1 \times 10^{-4}$.

6. The method of claim 1, wherein the considerable part of the substance which is transferred into the third state during one repetition of the electromagnetic signal is at least $1 \times 10^{-2}$.

7. The method of claim 1, wherein the interval of time for which the substance does return out of the fourth state neither into the first state nor the second state is longer than 1 minute.

8. The method of claim 1, wherein the interval of time for which the substance does return out of the fourth state neither into the first state nor the second state is longer than 10 minutes.

9. The method of claim 8, characterized in that the photon from the sample are registered with a one or two dimensional light sensor array onto which at least a part of the sample is imaged in a temporally invariant way.

10. The method of claim 9, wherein the electromagnetic signal comprises at least one continuous part.

11. The method of claim 1, wherein the interval of time for which the substance does return out of the fourth state neither into the first state nor the second state is longer than 1 hour.

12. The method of claim 1, wherein the substance does not return out of the fourth state neither into the first state nor the second state at all.

13. The method of claim 1, wherein the optimized value of the repetition interval of time is at least 1 μs.

14. The method of claim 1, wherein the electromagnetic signal is simultaneously directed at n separate areas of the sample to simultaneously optically measuring the sample in n measuring points.

15. The method of claim 14, wherein a repetition frequency of the electromagnetic signal at which it is directed at any areas of the sample in optically measuring the sample is at least 100 kHz/n.

16. The method of claim 1, wherein the sample is scanned with the electromagnetic signal directed at a spatially limited area of the sample.

17. The method of claim 16, wherein the value of the repetition interval of time is adjusted by means of adjusting a scanning velocity at which the sample is scanned with the electromagnetic signal.

18. The method of claim 1, wherein the electromagnetic signal includes excitation light for exciting the substance in the at least one area of the sample out of its first electronic state into its second electronic state and de-excitation light for de-exciting the substance in a spatially limited part of the at least one area of the sample out of its second electronic state.

19. The method of claim 1, wherein the electromagnetic signal includes excitation light for multi-photon excitation of the substance in the at least one area of the sample.

20. The method of claim 1, wherein the electromagnetic signal includes light for non-linear multi-photon scattering of the substance in the at least one area of the sample.

21. The method claim 1, wherein each repetition of the electromagnetic signal comprises a number of individual pulses of a same wavelength.

22. The method of claim 21, wherein the number of individual pulses of the same wavelength in each repetition of the electromagnetic signal is in a range of 1 to 100.

23. The method of claim 21, wherein the number of individual pulses of the same wavelength in each repetition of the electromagnetic signal is in a range of 1 to 100.

24. The method claim 1, wherein each repetition of the electromagnetic signal comprises a number of individual pulses of a same wavelength.

25. A method of optically measuring a sample including a substance which at least has a first electronic state and a second electronic state, the second electronic state being an excited electronic state of the substance, the second electronic state having a limited lifetime, and the substance emitting photons out of its second state, the method comprising the steps of:

selecting the substance in the sample from a group of substances having a lifetime of the second state of the substance which is longer than 0.1 ns and shorter than 10 ns;

repeatedly temporally directing an electromagnetic signal having a repetition interval of time at n separate spatially limited areas of the sample at one time to transfer the substance in each of these n areas of the sample out of its first electronic state into its second electronic state;

optimizing a value of the repetition interval of time of the signal with regard to a total yield of photons obtainable from a certain amount of the substance, the optimized value being at least 1 μs with the lifetime of the second state having an order of magnitude of 1 ns, the optimized value of the repetition interval of time of the signal being longer than a lifetime of a third state of the substance into which a considerable part of the substance in the areas of the sample of at least $1 \times 10^{-4}$ is transferred during one repetition of the electromagnetic signal in a parasitic way, the lifetime of the third state being longer than the lifetime of the second state of the substance by at least one order of magnitude, and the substance being transferable with the electromagnetic signal out of its third state into a fourth state out of which the substance does neither return into the first state nor into the second state for an interval of time which is longer than the 100-fold of the lifetime of the third state, and a repetition frequency of the electromagnetic signal at which it is directed at any areas of the sample in optically measuring the sample is at least 100 kHz/n; and detecting photons emitted by at least a part of the substance out of its second state.

26. The method claim 25, wherein each repetition of the electromagnetic signal comprises a number of individual pulses of a same wavelength.

27. The method of claim 25, wherein the electromagnetic signal includes excitation light for exciting the substance in each of the areas of the sample out of its first electronic state into its second electronic state and de-excitation light for de-exciting the substance in a spatially limited part of each of the areas of the sample out of its second electronic state.

28. A method of optically measuring a sample including a substance which at least has a first electronic state and a second electronic state, the second electronic state being an excited electronic state of the substance, the second electronic state having a limited lifetime, and the substance emitting photons out of its second state, the method comprising the steps of:

selecting the substance in the sample from a group of substances having a lifetime of the second state of the substance which is longer than 0.1 ns and shorter than 10 ns;

scanning the sample with an electromagnetic signal directed at least one spatially limited area of the sample to transfer the substance in the at least one spatially limited area of sample out of its first electronic state into its second electronic state;

optimizing a value of a repetition interval of time at which the electromagnetic signal is directed at the same area of the sample with regard to a total yield of photons obtainable from a certain amount of the substance, the optimized value being at least 0.1 us with the lifetime of the second state having an order of magnitude of 1 ns, and the optimized value of the repetition interval of time of the signal being longer than a lifetime of a third state of the substance into which a considerable part of the substance in the areas of the sample of at least $1\times10^{-4}$ is transferred during one repetition of the electromagnetic signal in a parasitic way, the lifetime of the third state being longer than the lifetime of the second state of the substance by at least one order of magnitude, and the substance being transferable with the electromagnetic signal out of its third state into a fourth state out of which the substance does neither return into the first state nor into the second state for an interval of time which is longer than the 100-fold of the lifetime of the third state; and detecting photons emitted by at least a part of the substance out of its second state.

29. The method of claim 28, wherein the electromagnetic signal comprises at least one continuous part.

30. The method of claim 28, wherein the electromagnetic signal includes excitation light for exciting the substance in the at least one spatially limited area of the sample out of its first electronic state into its second electronic state and de-excitation light for de-exciting the substance in a further spatially limited part of the at least one spatially limited area of the sample out of its second electronic state.

* * * * *